United States Patent [19]

Venkataram et al.

[11] Patent Number: 5,496,809
[45] Date of Patent: Mar. 5, 1996

[54] STABLE SOLUTIONS OF REBECCAMYCIN ANALOG

[75] Inventors: Ubrani V. Venkataram, Fayetteville; Miriam K. Franchini, Syracuse; Joseph B. Bogardus, Manlius, all of N.Y.

[73] Assignee: Bristol-Myers Squibb Co, New York, N.Y.

[21] Appl. No.: 349,608

[22] Filed: May 10, 1989

[51] Int. Cl.⁶ .............................. A61K 31/71; C07H 19/04
[52] U.S. Cl. .............................. 514/43; 514/42; 536/27.1
[58] Field of Search .............................. 536/22, 23, 22.1, 536/27.1; 514/42, 43

[56] References Cited

U.S. PATENT DOCUMENTS

| | | | |
|---|---|---|---|
| 4,785,085 | 11/1988 | Kaneko et al. | 532/22.1 |
| 4,808,613 | 2/1989 | Kaneko et al. | 514/42 |

OTHER PUBLICATIONS

Shriner et al. *The Systematic Identification of Organic Compounds*. John Wiley & Sons (New York: 1965), pp. 72–87.

Lehninger, A. L. *Biochemistry: The Molecular Basis of Cell Structure and Function*. Worth Publishers, Inc. (Johns Hopkins University, 1975), pp. 48–53.

*Primary Examiner*—Douglas W. Robinson
*Assistant Examiner*—Gary L. Kunz
*Attorney, Agent, or Firm*—Sandra M. Nolan

[57] ABSTRACT

Stable solutions of rebeccamycin analog consist essentially of (a) water, (b) 8-N-(diethylaminoethyl)rebeccamycin in an effective dosage amount, and (c) pharmaceutically acceptable acid such that the presence of a molar equivalence thereof would solubilize (b), said acid being present in excess of said molar equivalence to provide a stabilizing pH ranging from 3 to 4, preferably from 3.0 to 3.6. A preferred solution contains 10 mg/ml of the free base and tartaric acid in equimolar amount with the free base to provide a pH of 3.5. Preferably, the solution is prepared by forming a suspension of 8-N-(diethylaminoethyl)rebeccamycin in water and adding acid to provide a pH ranging from 3 to 4.

13 Claims, No Drawings

STABLE SOLUTIONS OF REBECCAMYCIN ANALOG

TECHNICAL FIELD

This invention is directed to stable solutions of the antitumor compound 8-N-(diethylaminoethyl)rebeccamycin and to a preferred method for forming such.

BACKGROUND OF THE INVENTION

Kaneko et al U.S. Pat. No. 4,785,085 discloses rebeccamycin analogs which include 8-N-(diethylaminoethyl)rebeccamycin which has the formula:

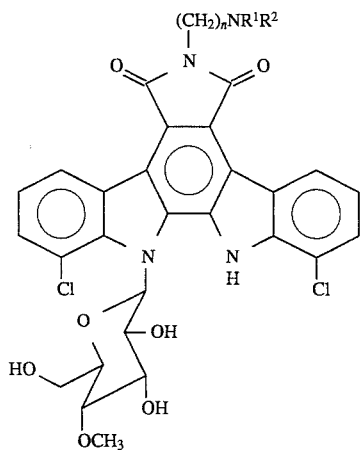

wherein n is 2 and $R^1$ and $R^2$ are each ethyl. The compound is referred to in Kaneko et al U.S. Pat. No. 4,785,085 as 6-(2-diethylaminoethyl)rebeccmycin and its preparation is described in Example 1 of the patent and its effectiveness to inhibit growth of tumors in experimental animal systems is shown in Table 3 of the patent. However, the compound is not sufficiently soluble in water when added thereto so as to form an aqueous injectable solution. Instead, it forms a suspension.

The technique of forming acid addition and base salts whereby the solubility of rebeccamycin analogs would be increased is suggested at column 9, lines 9 to 41 of Kaneko et al. The preparation of the hydrochloride salt of 8-N-(diethylaminoethyl)rebeccamycin is described in Example 2 of Kaneko et al where it is referred to as 6-(2-diethylaminoethyl)rebeccamycin hydrochloride and its effectiveness to inhibit growth of tumors in experimental animal systems is shown in Table 3 of the patent.

In respect to acid addition salts of 8-N-(diethylaminoethyl)rebeccamycin including the hydrochloride salt thereof, a problem encountered is that the crystalline acid addition salts, which contain one molar equivalent of acid reacted with the free base, when added to water in concentrations sufficient for use as, or dilution to, pharmaceutical dosage forms, do not form aqueous solutions which are sufficiently shelf stable. Rather, long term studies have revealed unusual physical instabilities over a period less than that which is considered acceptable for pharmaceutical compositions, namely at least 2 years at room temperature. These unexpected physical instabilities include gelling, precipitation, cloudiness, and formation of liquid crystalline phases which render solutions of the crystalline salts unsuitable for practical use as, or for dilution with water to provide, injectable solutions.

The object herein is to provide an aqueous solution of 8-N-(diethylaminoethyl)rebeccamycin for injection or for dilution for injection which is substantially chemically and physically stable over a period of at least two years at room temperature.

The term "stable" is used hereinafter to mean substantially chemically and physically stable over a period of at least two years at room temperature when protected from light (e.g. by screening out light with an opaque material or by housing the solution in amber glass containers), when it is not otherwise qualified. The term "substantially chemically stable" means that analysis indicates the presence of at least 95% by weight of 8-N-(diethylaminoethyl)rebeccamycin initially dissolved is still in solution. The term "substantially physically stable" means the substantial absence of formation of a gel, precipitate, cloudiness or liquid crystalline phase, or other particulate matter which would make the solution unsuitable for injection.

SUMMARY OF THE INVENTION

It has been discovered herein that the use of particular acids in certain amounts in conjunction with useful concentrations of 8-N-(diethylaminoethyl)rebeccamycin in water provide stable aqueous solutions of said concentrations of 8-N-(diethylaminoethyl)rebeccamycin. The acids are pharmaceutically acceptable acids such that one molar equivalent thereof would solubilize the 8-N-(diethyaminoethyl)rebeccamycin. An acid is used in an amount in excess of said molar equivalence to provide a pH less than 4. An acid used in a molar equivalent amount will not provide the benefits of the invention. Thus, crystalline acid addition salts per se formulated in aqueous solution will not provide stable solutions.

Besides being stable at room temperature, the solutions herein have enhanced solubility at low temperatures, e.g., refrigeration temperatures or cold conditions encountered during shipping or storage, etc.

The stable solutions herein consist essentially of:

(a) water, (b) 8-N-(diethylaminoethyl)rebeccamycin in an effective dosage amount and at a concentration up to 50 mg/ml of water, and (c) pharmaceutically acceptable acid such that the presence of a molar equivalence thereof would solubilize (b), said acid being present in excess of said molar equivalence to provide a stabilizing pH ranging from 3 to 4.

The term "effective dosage amount" is used herein to mean an antitumor effective amount when administered per se or after dilution.

The term "molar equivalent" or "molar equivalence" means that for 1.0 mole of 8-N-(diethylaminoethyl)rebeccamycin, 1.0 molar equivalent of an acid is required to fully neutralize the base. Therefore with a diprotic acid such as tartaric acid, 1.0 mole of 8-N-(diethylaminoethyl)rebeccamycin requires 0.5 mole acid for one molar equivalent of acid and more than 0.5 mole acid to provide acid in excess of the molar equivalence.

A preferred method for preparing the above stable aqueous solutions comprises the steps of:

(a) forming a suspension of 8-N-(diethylaminoethyl)rebeccamycin in water at a concentration of at least 1 mg/ml of water.

(b) adding pharmaceutically acceptable acid such that the presence of a molar equivalence thereof would solubilize the 8-N-(diethylaminoethyl)rebeccamycin present in the suspension formed in step (a), in an amount in excess of said molar equivalence to provide a stabilizing pH ranging from 3 to 4.

DETAILED DESCRIPTION

We turn firstly to the stable solutions herein.

The water component should be suitable for preparation of injectable solutions, e.g., Water for Injection, USP.

The 8-N-(diethylaminoethyl)rebeccamycin should normally be present in a concentration of at least 0.1 mg/ml of water, often in a concentration of least 1 mg/ml of water, or at least 5 mg/ml of water, as this concentration will provide, or can be diluted to, the range of antitumor effective injectable concentrations. The upper limit is that allowed by the solubilizing effect of the acid component (c) and is determined by the solubility of the acid addition salt of 8-N-(diethylaminoethyl)rebeccamycin with a molar equivalent of said acid. The concentration of 8-N-(diethylaminoethyl)rebeccamycin should not be such that crystallization occurs when the solution is exposed to refrigeration conditions, normally 2° to 8° C. The general upper limit of 50 mg/ml was selected to be above the highest contemplated dose for the drug projected from toxicity testing and allows for dilution to an effective dosage.

As indicated above, the acid component (c) must be pharmaceutically acceptable. This means that the acid component (c) should be one that does not contribute significantly to the toxicity of the free base.

The acid component (c) preferably is the one such that the acid addition salt thereof (formed from free base and a molar equivalent of acid) has a solubility in water at room temperature greater than 25 mg/ml. Pharmaceutically acceptable acid components (c) which meet this solubility criterion include, for example, L-(+)-tartaric, D,L-malic, L-(−)-malic, citric, L-(+)-lactic, lactobionic, methanesulfonic, phosphoric, pyroglutamic, succinic and sulfuric acids. The most preferred acid of these is L-(+)-tartaric acid.

As indicated above, the acid component (c) is present in excess of molar equivalence with (b) to provide a pH ranging from about 3 to about 4. The upper limit of about 4 must be met in order to provide a stable solution (i.e., physically stable). Although formulations below about pH of 3 are stable, such acidic pH's are not desirable for physiologic acceptability. Preferably component (c) is present to provide a pH ranging from about 3.0 to about 3.6 when the concentration of 8-N-(diethylaminoethyl)rebeccamycin is about 10 to 25 mg/ml of water.

Most preferably, tartaric acid is utilized as component (c) in an equimolar amount with the 8-N-(diethylaminoethyl)rebeccamycin. Where 8-N-(diethylaminoethyl)rebeccamycin is present at a concentration of 25 mg/ml of water, this provides a pH of 3.2. As is well known in the art, dilution of this composition with water will result in increase in solution pH toward neutrality. It should be noted that differences in purity can cause small pH variations despite the same concentration of active.

As indicated above, a preferred method for preparing the solution herein is to form a suspension of the 8-N-(diethylaminoethyl)rebeccamycin in water and then to add the acid component to provide the requisite pH. This is followed by stirring, e.g., for 5 to 15 hours at room temperature. Any slight cloudiness is readily removed by filtering.

Alternatively, the solutions herein can be made up by first adding the acid to water and then the 8-N-(diethylaminoethyl)rebeccamycin active, or by adding acid and active to a container and then adding water.

Methods known in the art such as heating, intense stirring, sonication, etc., can be used to enhance the rate of dissolution.

The solutions herein are also readily prepared by adding the acid addition salt to water (formed from acid such that the requisite initial solubility of 8-N-(diethylaminoethyl)rebeccamycin is provided) and then adjusting the pH to the 3–4 range using the same acid as is present in the acid addition salt or another acid meeting the criteria for component (c).

In therapeutic use for treating a mammalian host, for example an experimental animal host, affected by a malignant tumor, the solutions of the invention should be administered in an amount effective to inhibit the growth of the tumor, that is, in a tumor growth-inhibiting amount dosage. Generally, the tumor growth inhibiting amount will be in the range of about 0.1 to about 100 mg/kg of animal body weight per day. It is to be understood that the actual preferred dosage of compound will vary widely depending on the requirements of the animal being treated, the situs of the tumor, the type of the tumor, and the route of administration. Many factors that modify the action of the antineoplastic agent will be taken into account by one skilled in the art to which this invention pertains including, for example, age, body weight and sex, diet, time of administration, rate of excretion, condition of the host and severity of the disease. Optimal administration (or application) rates for a given set of conditions may be readily ascertained by those skilled in the art using conventional dosage determination tests.

The solutions herein may be used per se for injection if an injectable amount will provide the requisite dosage or may be diluted for administration if an injectable amount would provide too high a dosage. Dilution is readily carried out with Water for Injection USP, saline, 5% dextrose solution or the like. Injectable concentrations normally range from 0.1 to 50 mg/ml in terms of free base per ml of water.

The following examples are presented to illustrate representative embodiments of the invention and are not to be construed as limiting in scope.

Example I

A 12 mg/ml (free base per ml of water) solution was prepared from 249.2 mg of free base, i.e., 8-N-(diethylaminoethyl)rebeccamycin, 96.2% pure, 54.0 mg of L-(+)-tartaric acid and 20 ml of Sterile Water for Injection as follows: The free base was suspended in the water. Then the acid was added. Stirring was then carried out overnight at room temperature in a flint glass vial wrapped with aluminum foil to protect from light. The resulting slightly cloudy solution was then filtered through a 0.2 micron Acrodisc CR filter, resulting in a clear yellow solution. The formula represents a 1:1 molar ratio of free base to acid. The pH of the filtered solution was 3.6.

When solution is made similar to above except that 520.15 mg of free base and 112.6 mg of the tartaric acid is used, a solution is prepared containing 25 mg/ml (free base per ml of water) containing free base and tartaric acid in a 1:1 molar ratio and having a pH of 3.2.

Example II

A 10 mg/ml (free base per ml of water) solution was prepared from 10.40 g of 8-N-(diethylaminoethyl)rebeccamycin (96% pure), 2.26 g L-(+)-tartaric acid and USP Sterile Water for Injection, q.s. to 1000 ml as follows: The 8-N-(diethylaminoethyl)rebeccamycin was suspended in a portion (90% of that required) of the Water for Injection. Then the L-(+)-tartaric acid was added, and the suspension was stirred overnight forming a slightly cloudy solution. Water for Injection was then added, q.s. to 1000 ml, and the solution as aseptically filtered under nitrogen pressure through a Gelman Capsule Filter (P/N 12120) and collected in a sterile receiving vessel. The solution was aseptically filled into USP Type I flint glass ampules (10 ml/ampule). The ampules were flushed with sterile nitrogen gas and sealed. The solution contained free base and tartaric acid in a 1:1 molar ratio and had a pH of 3.5.

Testing by storage for 4 weeks at temperatures up to 56° C. provided no physical or chemical changes indicating a probable shelf life of at least 2 years when stored at 2°–30° C., protected from light.

For administration by intravenous infusion, the solution obtained can be diluted to, for example, 1 mg free base per ml of water with Water for Injection USP or 5% Dextrose solution. The diluted solutions were observed to be physically stable for 24 hours under normal room-light condition.

Example III

Solutions containing 25 mg of 8-N-(diethylaminoethyl)rebeccamycin per ml of water were made up with acids and molar ratios of acid to base as set forth below. These were stored for 4 weeks at 56° C. protected from light with the following results:

| Acid | Physical Stability pH Results | % Base Remaining In Solution |
|---|---|---|
| L-(+)-tartaric acid (1 acid: 1 base) | 3.2 No changes observed | 96 |
| L-(+)-tartaric acid (1 acid: 2 base) | 5.1 Forms a gel | not analyzed |
| L-(−)-malic acid (1.7 acid: 1 base) | 3.4 No changes observed | 100 |
| L-(−)-malic acid (1 acid: 1 base) | 3.8 Forms precipitate | 94 |
| Phosphoric acid (1.2 acid: 1 base) | 3.5 No changes observed | 99 |
| Phosphoric acid (1 acid: 1 base) | 4.5 Forms a cloudy solution | 98 |
| L-(+)-lactic acid (2.5 acid: 1 base) | 3.6 No changes observed | 100 |
| Succinic acid (4 acid: 1 base) | 3.5 No changes observed | 99 |
| Lactobionic acid (3 acid: 1 base) | 3.3 No changes observed | 102 |

The above indicates the criticality of pH in obtaining physical stability. No physical changes resulting in the above testing predicts physical stability for at least 2 year when stored at 2 to 30° C., protected from light.

The above solutions were also tested in freeze/thaw tests by cycling between −20° C. and room temperature 5 times during a week. The solutions that were observed to be physically stable above were also physically stable in this test indicating that said solutions can be refrigerated or even frozen without deleterious results.

Example IV

Solution of 8-N-(diethylaminoethyl)rebeccamycin made up with tartaric acid was tested for antitumor activity against transplanted mouse leukemia P-338 according of Geran et al reported in *Cancer Chemother. Repts.*, 3, 1–103 (1972). The screening procedures involved administration of test compound intraperitonially (IP) to CDF1 female mice (18 to 22 grams) infected with $1 \times 10^6$ ascites cells intraperitonially, and intravenously (IV) to CDF1 female mice (18 to 22 Grams) infected with $1 \times 10$ ascites cells intravenously. Drug therapy was started on Day 1 (date of implant) and consisted of 1 injection per day for 5 successive days. Using a solution of 8-N-(diethylaminoethyl)rebeccamycin at a concentration of 25 mg free base per ml of water and tartaric acid in a 1:1 molar ratio with the free base, dosages were made up by dilution so as to be contained in 0.5 ml for IP injection and in 0.2 ml for IV injection and are denoted "Invention" below. In the results below, MST stands for median survival time in days; % T/C is the median survival time of the test animals divided by the median survival time of control animals ×100; and AWC is average weight change at Day 5 in Grams. Mitomycin C is included for comparison purposes. The results for IP testing were as follows:

| Drug | Dose, IP mg/kg/inj | MST | % T/C | AWC |
|---|---|---|---|---|
| Mitomycin C | 4.8 | 20.5 | 205 | −0.6 |
|  | 3.2 | 20.5 | 205 | −0.1 |
| Invention | 24 | 15.5 | 155 | −0.8 |
|  | 18 | 16.5 | 165 | −1.0 |
|  | 12 | 15.0 | 150 | 0.1 |
| Control |  | 10 | 100 | 1.6 |

The results for IV testing were as follows:

| Drug | Dose, IP mg/kg/inj | MST | % T/C | AWC |
|---|---|---|---|---|
| Mitomycin C | 4.8 | 12.0 | 160 | −0.1 |
|  | 3.2 | 11.0 | 147 | −0.4 |
|  | 1.6 | 9.5 | 127 | 0.4 |
| Invention | 96 | 12.5 | 167 | −0.7 |
|  | 80 | 12.0 | 160 | 0.3 |
|  | 64 | 11.0 | 147 | 0.3 |
|  | 48 | 10.0 | 133 | 1.4 |
| Control |  | 7.5 | 100 | 1.4 |

The above indicates the tartaric acid containing solutions of the instant invention possess antineoplastic activity.

Variations will be evident to those skilled in the art. Therefore, the scope of the invention is intended to be defined by the claims.

What is claimed is:

1. A stable solution consisting essentially of
   (a) water,
   (b) 8-N-(diethylaminoethyl)rebeccamycin in an effective dosage amount at a concentration up to 50 mg/ml of water, and
   (c) a pharmaceutically acceptable acid, a molar equivalence of which will solubilize compound (b), said acid being present in said solution in an amount in excess of said molar equivalence to provide a stabilizing pH for said solution ranging from 3.0 to 3.6.

2. A stable solution as recited in claim 1 wherein said acid is one such that the acid addition salt thereof with 8-N-(diethylaminoethyl)rebeccamycin has a solubility in water at room temperature greater than 25 mg/ml.

3. A stable solution as recited in claim 2 wherein said acid is selected from the group consisting of L-(+)-tartaric, D,L-malic, L-(−)-malic, citric, L-(+)-lactic, lactobionic, methanesulfonic, phosphoric, pyroglutamic, succinnic and sulfuric acids.

4. A stable solution as recited in claim 3 wherein said acid is selected from the group consisting of L-(+)-tartaric acid, L-(−)-malic acid, phosphoric acid, L-(+)-lactic acid, succinnic acid and lactobionic acid.

5. A stable solution as recited in claim 4 wherein said acid is L-(+)-tartaric acid.

6. A stable solution as recited in claim 5 wherein the L-(+)-tartaric acid and the 8-N-(diethylaminoethyl)rebeccamycin are present in equimolar amounts.

7. A stable solution as recited in claim 6 wherein the 8-N-(diethylaminoethyl)rebeccamycin is present at a concentration of 10 mg/ml of water.

8. A stable solution as recited in claim 6 wherein the 8-N-(diethylaminoethyl)rebeccamycin is present at a concentration of 25 mg/ml of water.

9. Method of preparing a stable aqueous solution of 8-N-(diethylaminoethyl)rebeccamycin, said method comprising the steps of:

(a) forming a suspension of 8-N(diethylaminoethyl)rebeccamycin in water at a concentration of at least 1 mg/ml of water, (b) adding a pharmaceutically acceptable acid to said suspension, a molar equivalence of which will solubilize the 8-N(diethylaminoethyl)rebeccamycin present in the suspension formed in step (a), said acid being added in an amount in excess of said molar equivalence to provide a stabilizing pH for said solution ranging from 3.0 to 3.6.

10. A method as recited in claim 9 wherein said acid is L-(+)-tartaric acid.

11. Method as recited in claim 10 wherein said acid is added in an equimolar amount to the 8-N-(diethylaminoethyl)rebeccamycin.

12. Method as recited in claim 11 wherein the concentration of 8-N- (diethylaminoethyl) rebeccamycin in step (a) is 10 mg/ml.

13. Method as recited in claim 11 wherein the concentration of 8-N-(diethylaminoethyl)rebeccamycin in step (a) is 25 mg/ml.

* * * * *